United States Patent [19]

Tohge et al.

[11] Patent Number: 5,245,318
[45] Date of Patent: Sep. 14, 1993

[54] PARTICLE ANALYZING APPARATUS HAVING PRESSURE CONTROL SYSTEM

[75] Inventors: Yoshiyuki Tohge; Naoki Yuguchi, both of Yokohama, Japan

[73] Assignee: Canon Kabushiki Kaisha, Tokyo, Japan

[21] Appl. No.: 990,922

[22] Filed: Dec. 15, 1992

Related U.S. Application Data

[63] Continuation of Ser. No. 780,399, Oct. 23, 1991, abandoned, which is a continuation of Ser. No. 680,649, Apr. 2, 1991, abandoned, which is a continuation of Ser. No. 221,097, Jul. 19, 1988, abandoned.

[30] Foreign Application Priority Data

| Jul. 24, 1987 | [JP] | Japan | 62-185841 |
| Sep. 30, 1987 | [JP] | Japan | 62-246291 |
| Sep. 30, 1987 | [JP] | Japan | 62-246292 |
| Sep. 30, 1987 | [JP] | Japan | 62-246297 |

[51] Int. Cl.$^5$ ............... G08B 21/00; G01N 15/02
[52] U.S. Cl. .................. 340/611; 340/607; 356/338; 324/71.4; 73/199
[58] Field of Search ............... 340/607, 611, 626, 627; 356/337-339; 324/71.4, 71.1; 73/861.52, 861.62, 861.42, 195, 199

[56] References Cited

U.S. PATENT DOCUMENTS

| 4,178,103 | 12/1979 | Wallace | 356/338 |
| 4,325,706 | 4/1982 | Gershman et al. | 356/39 |
| 4,367,043 | 1/1983 | Sweet et al. | 356/338 |
| 4,503,385 | 3/1985 | Haynes | 324/71.4 |
| 4,525,666 | 6/1985 | Groves | 324/71.4 |
| 4,596,036 | 6/1986 | Nogren et al. | 356/336 |
| 4,606,631 | 8/1986 | Anno et al. | 356/338 |
| 4,761,074 | 8/1988 | Kohsaka et al. | 356/338 |
| 4,781,459 | 11/1988 | Suzuki | 356/339 |

Primary Examiner—Edward L. Coles, Sr.
Assistant Examiner—Jill Jackson
Attorney, Agent, or Firm—Fitzpatrick, Cella, Harper & Scinto

[57] ABSTRACT

A particle analyzing apparatus having sample liquid pressurizing means for pressurizing sample liquid containing therein particles to be examined and supplying it to a portion to be examined, sheath liquid pressurizing means for pressurizing sheath liquid and supplying it to the portion to be examined in such a manner as to surround the sample liquid, a pressure sensor provided in the flow path of the sheath liquid between the sheath liquid pressurizing means and the portion to be examined, pressure control means for controlling the pressure value of the sheath liquid pressurizing means so that the output of the pressure sensor becomes constant, and means for applying light to the portion to be examined and photometering light emitted from the particles to be examined to thereby effect particle analysis.

50 Claims, 2 Drawing Sheets

PARTICLE ANALYZING APPARATUS HAVING PRESSURE CONTROL SYSTEM

This application is a continuation of application Ser. No. 07/780,399, filed Oct. 23, 1991, which is a continuation of Ser. No. 07/680,649, filed Apr. 2, 1991, which is a continuation of Ser. No. 07/221,097, filed Jul. 19, 1988, all now abandoned.

BACKGROUND OF THE INVENTION

1. Field of the Invention

This invention relates to a particle analyzing apparatus, for example, a so-called flow sightmeter in which particles to be examined are passed to a flow cell unit and light is applied to the passing particles to be examined and scattered light and fluorescence emitted from the particles to be examined are photometered, whereby analysis of the particles to be examined is effected.

2. Related Background Art

A flow sightmeter is an apparatus in which sample liquid which is a cell-suspended solution and sheath liquid outside thereof (for example, physiological saline solution) flow at a high speed with a predetermined pressure difference imparted thereto, the flow thereof is hydrodynamically converged, a laser light is applied to particles to be examined flowing to the converged position one by one, and scattered light and fluorescence from the particles to be examined are detected by a photodetector to thereby analyze the property, structure, etc. of the particles to be examined. Such an apparatus is used in the fields of cytology, blood science, immunology, genetics, etc.

The sample liquid and the sheath liquid are stored in discrete containers, and the air in the containers is pressurized by a pressurizing system such as a compressor or a nitrogen gas bomb and each liquid is directed to a flow cell which is a portion to be examined. At this time, the sample liquid is wrapped, or surrounded, in the sheath liquid and is hydrodynamically converged, and the particles to be examined in the sample liquid form in line one by one and pass through the flow cell unit. The flow diameter of the sample liquid is regulated with the particle diameter of the particles to be examined and the measurement speed taken into account, and this regulation is accomplished by regulating the pressure of the air pressurized in the containers in which the sheath liquid and the sample liquid are contained, respectively.

However, there arises the problem that the flow diameter of the sample liquid changes in spite of the pressure of the air pressurized in the containers in which the sheath liquid and the sample liquid are contained being set once.

A first cause of this problem is that as measurement is started, the liquids are consumed and the liquid levels thereof lower, whereby the pressures of the liquids directed to the flow cell are reduced. Particularly, unlike the sample liquid which is interchanged during each measurement, the consumption of the sheath liquid which is used in each measurement is great. U.S. Pat. No. 4,503,385 tries to solve this problem by providing a storing portion and a preliminary chamber for the sheath liquid and keeping the liquid level of the sheath liquid constant, but the apparatus of this patent is somewhat complex in structure and has a problem in stability.

A second cause is that where a filter (particularly for the sheath liquid) for removing impurities is used in the flow path leading from the container to the flow cell, this filter becomes gradually clogged each time measurement is repeated and the pressure loss resulting from such clogging reduces the pressure of the liquid directed from the filter to the flow cell.

SUMMARY OF THE INVENTION

It is a first object of the present invention to provide a particle analyzing apparatus in which a pressure sensor is provided in the flow path of sheath liquid to thereby ensure a constant flow diameter of sample liquid.

It is a second object of the present invention to provide a particle analyzing apparatus in which the amount of remaining sheath liquid can be detected.

It is a third object of the present invention to provide a particle analyzing apparatus in which clogging of a filter can be detected.

It is a fourth object of the present invention to provide a particle analyzing apparatus in which detection of the amount of remaining sheath liquid and detection of the clogging of a filter can be accomplished at the same time.

DESCRIPTION OF THE PREFERRED EMBODIMENTS

Figure 1:
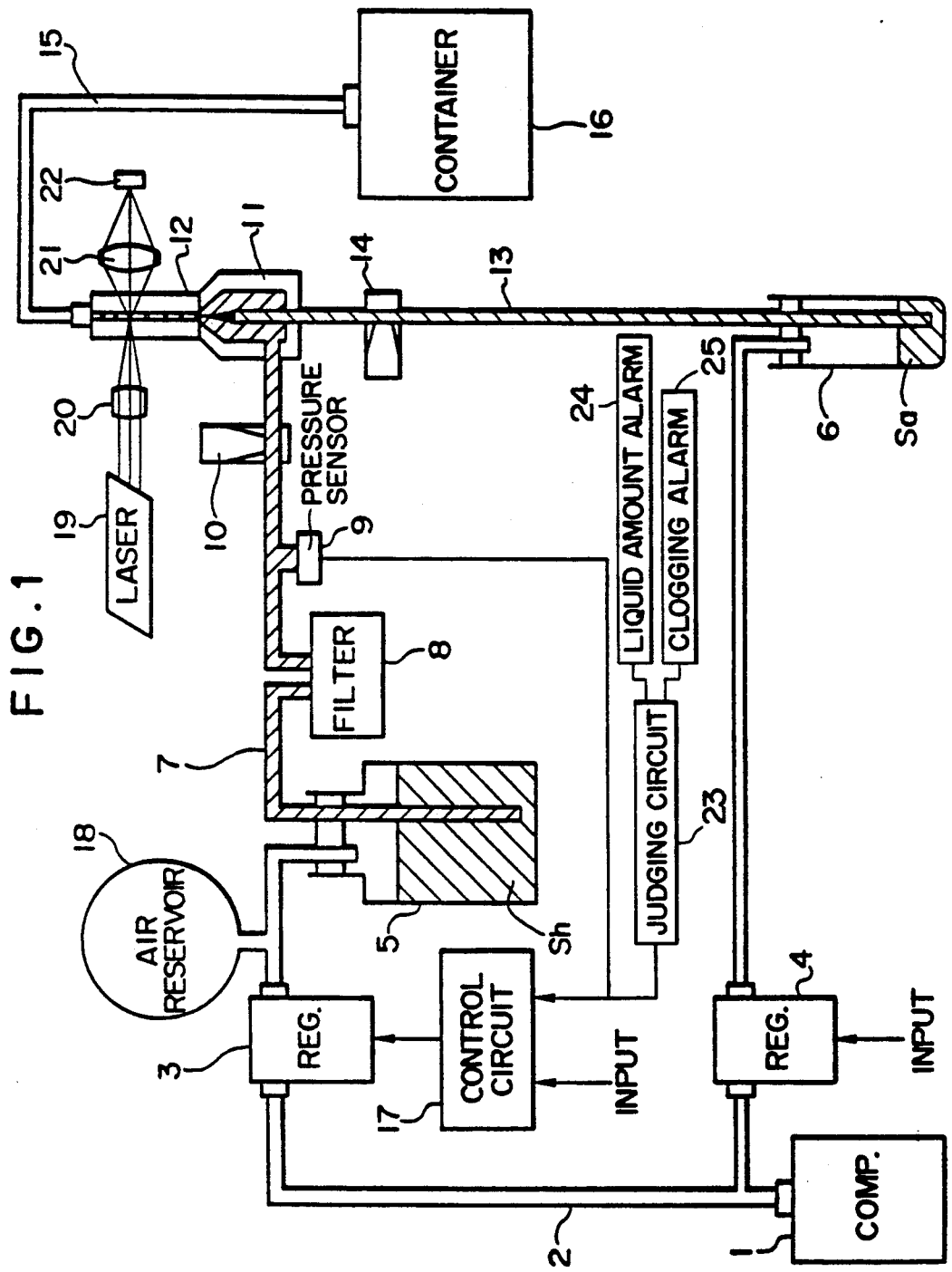
FIG. 1 shows the construction of an embodiment of a particle analyzing apparatus according to the present invention.

Referring to FIG. 1, the reference numeral 1 designates a compressor which is a compressed air generating source, and an air tube 2 connected to this compressor branches off into two branches. The branches of the air tube 2 are connected to a sheath liquid container 5 and a sample liquid container 6, respectively, storing therein sheath liquid Sh and sample liquid Sa, respectively, in an air-tight manner, through electrical type regulators 3 and 4 for pressure regulation provided for the sheath liquid and the sample liquid, respectively. An air reservoir 18 provided in the flow path between the regulator 3 and the sheath liquid container 5 makes delicate pressure control possible. A sheath tube 7 immersed in the sheath liquid Sh in the sheath liquid container 5 is directed into a nozzle 11 through an impurity removing filter 8, a pressure sensor 9 and a sheath liquid inflow control valve 10. The pressure sensor 9 has its sensor surface set upward so that no bubble may enter thereinto. If the sheath liquid is already cleaned sheath liquid, the filter 8 may be eliminated. A sample tube 13 immersed in the sample liquid Sa in the sample liquid container 6 is directed into the nozzle 11 through a sample liquid inflow control valve 14 and the tip end portion thereof is directed to a flow cell 12 connected to the upper end of the nozzle 11. The sample liquid and the sheath liquid flow against gravity so that bubbles unexpectedly produced in the flow cell 12 may flow with fluid and be quickly removed. A waste liquid tube 15 is connected to the upper end of the flow cell 12 and the other end thereof is connected to a waste liquid container 16. An electrical signal of set pressure is input from the outside to a control circuit 17, and the output of the pressure sensor 9 is further input thereto, and the output therefrom is input to the electrical type regulator 3. When the liquid level of the sheath liquid Sh falls or when the filter 8 is clogged and the output of the pressure sensor 9 drops below a standard value, the internal air pressure in the sheath liquid container 5 is enhanced by the regulator 3 and the output of the pressure sensor 9 is brought into coincidence with the standard value, whereby pressure control is accomplished. An electrical signal for setting the sample pressure is input from the outside to the electrical type regulator 4. Input values input from the outside to the control circuit 17 and the regulator 4 have their optimum values selected and set by such conditions as the kind of particles, the size of the particles and the velocity of flow.

The reference numeral 19 designates a laser for measurement, the reference numeral 20 denotes a condensing lens, the reference numeral 21 designates a light-receiving lens, and the reference numeral 22 denotes a photodetector. The set of the light-receiving lens and the photodetector is set in the direction of application of the laser and on the opposite side of the flow cell 12 therefrom.

To keep the diameter of the sample flow constant, it is more preferable to effect the pressure control of the pressure value of the sample liquid as well as the pressure control of the pressure value of the sheath liquid as described above. However, if a pressure sensor is provided in the flow path between the sample liquid container and the flow cell, part of the sample liquid will adhere to the pressure sensor and when different sample liquid is used in another measurement effected subsequently, the sample liquid which has adhered to the pressure sensor will mix with the different sample liquid, and this will hinder the measurement. However, as compared with the drop of the liquid level of the sheath liquid when measurement of a great quantity is effected, the drop of the liquid level of the sample liquid which is interchanged during each measurement is very slight and therefore, the influence of the drop of the liquid level of the sample liquid upon the variation in the diameter of the sample flow is considered to be almost null. Consequently, as in the embodiment, sufficient accuracy is obtained by the pressure control of only the pressure value of the sheath liquid.

Embodiment 2

Description will now be made of a method of detecting the amount of remaining sheath liquid.

The pressure value applied to the sheath liquid container 5 in the initial state before measurement is started, that is, when the sheath liquid container is full of the sheath liquid, is a predetermined value $P_0$, but the pressure value increases as the sheath liquid decreases. Consequently, the liquid level of the sheath liquid can be detected by watching the increment of the pressure signal value supplied from the control circuit 17 to the electrical type regulator 3 for sheath liquid which corresponds to the pressure value, from the signal value corresponding to said predetermined value when the sheath liquid container is full of the sheath liquid. The liquid level of the sheath liquid can also be detected by watching the increment not from the signal value corresponding to said predetermined value when the sheath liquid container is full of the sheath liquid, but from the initial value when the sheath liquid container is not full of the sheath liquid (this initial value can be detected from the pressure signal value in the initial state). The liquid level is detected in both instances by connecting a judging circuit 23 as shown in FIG. 1 to the control circuit. When this liquid level becomes lower than a certain level, a warning of the insufficiency of the amount of remaining sheath liquid is given by the alarm 24 or the operation of the apparatus is stopped.

Embodiment 3

Description will now be made of a method of detecting the clogging of the filter 8.

Figure 2:
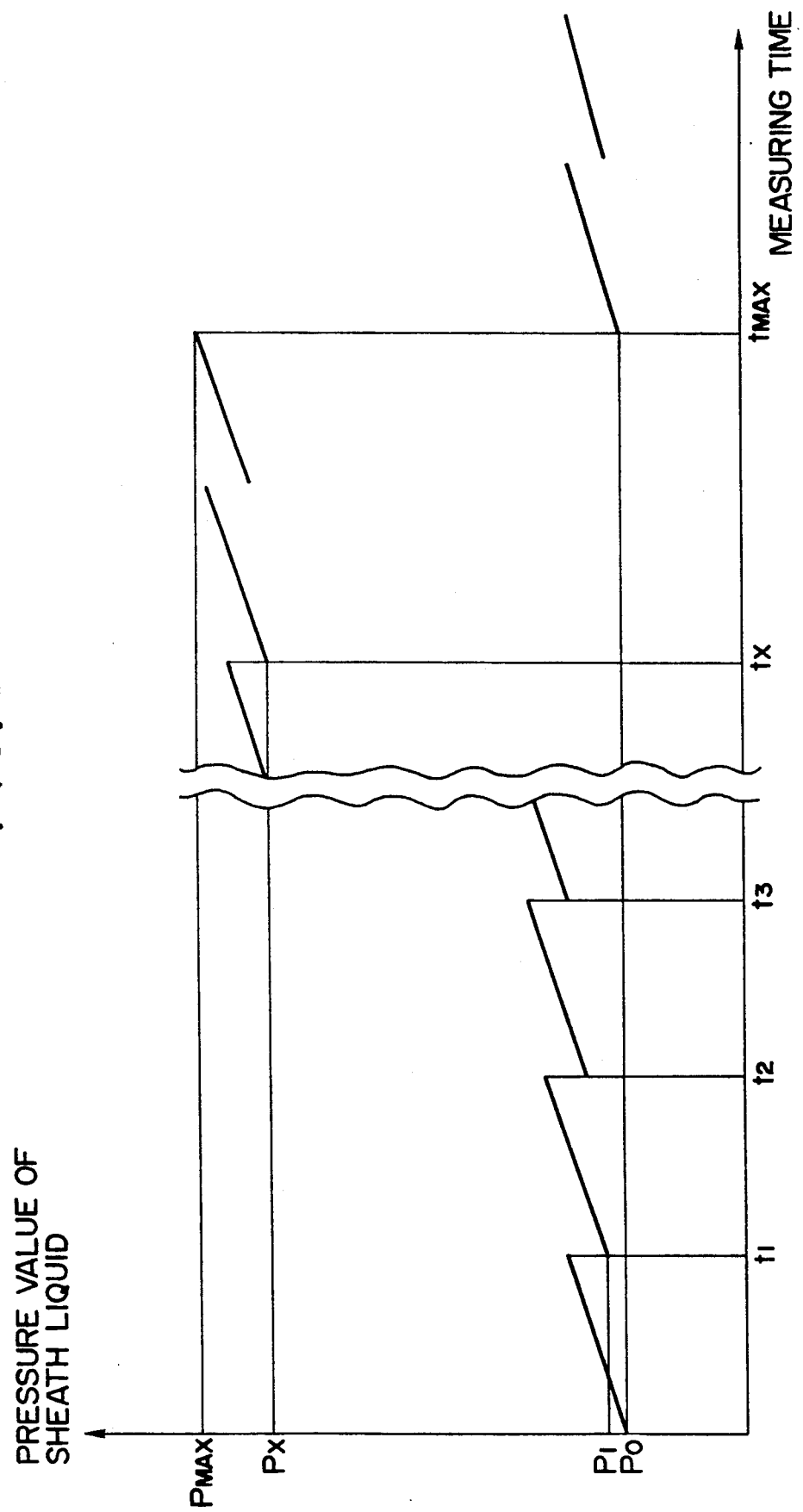
FIG. 2 is a graph showing variations in the pressure value in a sheath liquid container with the lapse of the measuring time.

FIG. 2 is a graph showing how the pressure value of the sheath liquid changes with the lapse of the measuring time. The judging circuit 23 is also used to detect whether the filter 8 is clogged. $P_0$ is the pressure value when the filter 8 is not clogged and the sheath liquid container is full of the sheath liquid. The progress of the clogging of the filter 8 is sufficiently slow as compared with the speed of decrease in the sheath liquid and therefore, the progress of the clogging of the filter 8 is very slight at a time $t_1$ when the sheath liquid assumes a caution liquid level. Consequently, the pressure value $P_1$ when the sheath liquid is supplied at the time $t_1$ to fill up the sheath liquid container rises slightly as compared with $P_0$. The pressure value $P_x$ when measurement has been repeated and the clogging of the filter 8 has progressed is considerably great relative to $P_0$. When the clogging progresses further and exceeds the caution value $P_{MAX}$, 10 a warning of the clogging of the filter is given by an alarm 25 as shown in FIG. 1 to call the operator's attention to the interchange of the filter 8. After the filter has been interchanged, the pressure value restores $P_0$ if the sheath liquid container is full of the sheath liquid, and what has been described above is repeated.

As can be seen from FIG. 2, the pressure value is increased also by a decrease in the sheath liquid, but such increase is slight as compared with the increase in the pressure value when the clogging of filter 8 has progressed, and the frequency with which the sheath liquid is supplied is much greater than the frequency with which the filter 8 is interchanged and therefore, the increase in the pressure value caused by the decrease in the sheath liquid is relatively small. So, the clogging of the filter 8 is judged by the judging circuit 23 to determine whether the pressure signal value supplied from the control circuit 17 to the electrical type regulator 3 for sheath liquid which corresponds to the pressure value in the sheath liquid container has exceeded the caution value $P_{MAX}$. When the clogging of the filter 8 is detected, a warning for calling the operator's attention to the interchange of the filter is given by alarm 25 or the operation of the apparatus is stopped.

Embodiment 4

Description will now be made of a method of distinguishing between and detecting a reduction in the pressure on the pressure sensor resulting from the clogging of the filter 8 and a reduction in the pressure resulting from a decrease in the sheath liquid.

The clogging of the filter 8, as previously described, is judged by the judging circuit 23 to determine whether the pressure value of the sheath liquid has exceeded the caution value $P_{MAX}$. Also, the amount of remaining sheath liquid can be judged via the judging circuit by memorizing the initial pressure values $P_0$, $P_1$, . . . when the sheath liquid container has been made full of the sheath liquid and seeing the difference thereof from the pressure value being measured. When this difference reaches the increment of the pressure value during the time from after the sheath liquid container is full of the sheath liquid until the sheath liquid assumes the caution liquid level, a warning of the amount of remaining sheath liquid is given by the alarm 24 to call the operator's attention to the supply of the sheath liquid.

The interchange of the filter resulting from the clogging thereof is sufficiently less frequent than the frequency with which the sheath liquid must be supplied because of the decreased amount of remaining sheath liquid and the pressure loss resulting from the clogging of the filter is sufficiently great and therefore, the two can be readily distinguished between.

Now, description has hitherto been made on the premise that when the sheath liquid is to be supplied, the sheath liquid is poured into the sheath liquid container until the container reaches full of, but there is conceivable a case where measurement is started from a state in which the sheath liquid container is not full of the sheath liquid or a case where the sheath liquid, if supplied, is not poured up to the upper limit. In these cases, there occurs the inconvenience that no warning is given even if the sheath liquid decreases. So, there would occur to mind a method of detecting the amount of remaining sheath liquid before starting measurement, displaying that the sheath liquid has decreased from its full state if the sheath liquid container is not full of the sheath liquid and thereby calling the user's attention to the supply of the sheath liquid, or a method of pre-correcting a predetermined pressure increment up to the caution liquid level in the case where the initial state is the state of fullness, in conformity with the liquid level of the sheath liquid decreased from the state of fullness.

As the former method of detecting whether the sheath liquid container before measurement is started is full of the sheath liquid, the sheath liquid inflow control valve 10 is closed and the sheath liquid is pressurized to a predetermined value (for example, the atmospheric pressure) by the electrical type regulator 3 for sheath liquid to detect whether the pressure value on the pressure sensor 9 is a predetermined value corresponding to said predetermined value or less, whereby whether the sheath liquid container is full of the sheath liquid is deduced. When there is a flow in the fluid as during measurement, there is a pressure loss in the filter 8, but when there is no flow in the fluid, there is no pressure loss in the filter 8 and therefore, no problem arises. Thus, even if an exclusive sensor (for example, a float) or the like is not provided, it is possible to detect whether the sheath liquid container before measurement is started is full of the sheath liquid. It is possible not only to judge whether the sheath liquid container is full of the sheath liquid by the use of the value of the pressure sensor 9, but also to find the actual liquid level of the sheath liquid by obtaining the exchange table of the value of the pressure sensor 9 and the actual liquid level.

Description will hereinafter be made of the latter method of correcting the predetermined pressure increment from the liquid level of the sheath liquid decreased from the state of fullness to the caution liquid level. It is possible to calculate the initial liquid level of the sheath liquid before measurement is started, from the pressure value of the pressure sensor 9 when the sheath liquid inflow control valve 10 is closed, by the above-described method. So, the initial liquid level is found by the above-described method before measurement is started, and the increment $\Delta P$ (a predetermined value) of the pressure value corresponding to that during the time from after the sheath liquid has filled up the sheath liquid container until it assumes the caution liquid level is corrected to the increment $\Delta P'$ of the pressure value corresponding to that during the time from after the sheath liquid is at the initial liquid level (the state of non-fullness) until it assumes the caution liquid level. $\Delta P'$ can be found by the calculation of (the liquid level difference from the initial liquid level to the caution liquid level)÷(the liquid level difference from the full liquid level to the caution liquid level) $\times \Delta P$. For example, if the liquid level difference from the initial liquid level to the caution liquid level is one-third of that of the full liquid level, the corrected value $\Delta P'$ of the increment of said pressure value is $\Delta P/3$. Thus, even though measurement is not started after the sheath liquid container has been made full of the sheath liquid, it is possible to exactly warn the operator of a decrease in the sheath liquid or stop the operation of the apparatus when the predetermined caution liquid level has been assumed.

The present invention is also applicable to a so-called jet-in-air type flow sightmeter, i.e., an apparatus in which a flow is converged in the air and a laser light is applied thereto to thereby effect particle analysis. In addition, the present invention is applicable to a particle counter or the like as a matter of course.

We claim:

1. A particle analyzing apparatus having a pressure control device, comprising:

particle receiving means for receiving particles to be examined;

sample supplying means for supplying sample liquid containing particles therein to be examined to said particle receiving means;

a sheath liquid container for storing sheath liquid therein;

sheath liquid supplying means for supplying the sheath liquid in said sheath liquid container to said particle receiving means;

convergent stream forming means for generating a thin flow of the sample liquid surrounded by the sheath liquid, with particles included in the sample liquid being individually separated and flowing through said particle receiving means;

filter means provided in a flow path between said sheath liquid container and said particle receiving means for removing impurities contained in the sheath liquid;

control means, including a pressure sensor, for controlling pressure of said sheath liquid supplying means so that an output of said pressure sensor is a predetermined value so as to maintain a constant diameter of the converged thin flow;

signalling means for measuring a level of the sheath liquid in said sheath liquid container and for signalling said control means when the level of the sheath liquid reaches a predetermined level; and measuring means for measuring a diameter of a particle flowing in the converged thin flow at said particle receiving means.

2. A particle analyzing apparatus according to claim 1, wherein said sheath liquid supply means includes pressure regulating means for pressurizing said sheath liquid container, and said signalling means signals said control means when a relative difference between a pressure level applied to said sheath liquid container being filled to capacity with the sheath liquid and a pressure level applied to said sheath liquid container filled to less than capacity becomes higher than a predetermined first value.

3. A particle analyzing apparatus according to claim 2, wherein said measuring means includes a laser source and optically measures the particles to be examined.

4. A particle analyzing apparatus having a pressure control device, comprising:
   particle receiving means for receiving particles to be examined;
   sample supplying means for supplying sample liquid containing particles therein to be examined to said particle receiving means;
   a sheath liquid container for storing sheath liquid therein;
   sheath liquid supplying means for supplying the sheath liquid in said sheath liquid container to said particle receiving means;
   convergent stream forming means for generating a thin flow of the sample liquid surrounded by the sheath liquid, with particles included in the sample liquid being individually separated and flowing through said particle receiving means;
   filter means provided in a flow path between said sheath liquid container and said particle receiving means for removing impurities contained in the sheath liquid;
   control means, including a pressure sensor, for controlling pressure of said sheath liquid supplying means so that an output of said pressure sensor is a predetermined value so as to maintain a constant diameter of the converged thin flow;
   signalling means for measuring a clogging level of said filter means and producing a warning signal when the clogging level reaches a predetermined warning level; and
   measuring means for measuring a diameter of a particle flowing in the converged thin flow at said particle receiving means.

5. A particle analyzing apparatus according to claim 4, wherein said sheath liquid supplying means includes pressure regulating means for pressurizing said sheath liquid container, and said signalling means produces the warning signal when an absolute value of the pressure applied to said sheath liquid container becomes higher than a predetermined level.

6. A particle analyzing apparatus according to claim 4, wherein said measuring means includes a laser source and optically measures the particles to be examined.

7. A particle analyzing apparatus having a pressure control device, comprising:
   particle receiving means for receiving particles to be examined;
   sample supplying means for supplying sample liquid containing particles therein to be examined to said particle receiving means;
   a sheath liquid container for storing sheath liquid therein;
   sheath liquid supplying means for supplying the sheath liquid in said sheath liquid container to said particle receiving means;
   convergent stream forming means for generating a thin flow of the sample liquid surrounded by the sheath liquid, with particles included in the sample liquid being individually separated and flowing through said particle receiving means;
   filter means provided in a flow path between said sheath liquid container and said particle receiving means for removing impurities contained in the sheath liquid;
   control means, including a pressure sensor, for controlling pressure of said sheath liquid supplying means so that an output of said pressure sensor is a predetermined value so as to maintain a constant diameter of the converged thin flow;
   signalling means for measuring a level of the sheath liquid in said sheath liquid container and a clogging level of said filter means and for producing a warning signal when either one of said sheath liquid level and said clogging level reaches a predetermined warning level; and
   measuring means for measuring a diameter of a particle flowing in the converged thin flow at said particle receiving means.

8. A particle analyzing apparatus according to claim 7, wherein said sheath liquid supplying means includes pressure regulating means for pressurizing said sheath liquid container, and said signalling means produces a first warning signal of liquid shortage when a relative difference between a pressure level applied to said sheath liquid container being filled to capacity with the sheath liquid and a pressure level applied to said sheath liquid container filled to less than capacity becomes higher than a first predetermined value and a second warning signal of filter clogging when an absolute value of pressure applied to said sheath liquid container becomes higher than a second predetermined level.

9. A particle analyzing apparatus according to claim 8, wherein said measuring means includes a laser source and optically measures the particles to be examined.

10. A particle analyzing apparatus having a pressure control device, comprising:
    particle receiving means for receiving particles to be examined;
    sample supplying means for supplying sample liquid containing particles therein to be examined to said particle receiving means;
    a sheath liquid container for storing sheath liquid therein;
    sheath liquid supplying means for supplying the sheath liquid in said sheath liquid container to said particle receiving means;
    convergent stream forming means for generating a thin flow of the sample liquid surrounded by the sheath liquid, with particles included in the sample liquid being individually separated and flowing through said particle receiving means;
    filter means provided in a flow path between said sheath liquid container and said particle receiving means for removing impurities contained in the sheath liquid;
    control means, including a pressure sensor, for controlling pressure of said sheath liquid supplying means so that an output of said pressure sensor is a predetermined value so as to maintain a constant diameter of the converged thin flow;
    a control valve provided between said filter means and said particle receiving means for controlling flow of the sheath liquid; and
    measuring means for measuring a diameter of a particle flowing in the converged thin flow at said particle receiving means.

11. A particle analyzing apparatus according to claim 10, wherein said sheath liquid supplying means includes pressure regulating means for pressurizing said sheath liquid container, and further comprising means for measuring a sheath liquid level on the basis of an output of said pressure sensor obtained when said control valve is closed and a predetermined level of pressure is applied to said sheath liquid container.

12. A particle analyzing apparatus according to claim 11, further comprising means for judging whether said sheath liquid container is filled with said sheath liquid by measuring the liquid level in said sheath liquid container previous to the measurement of the sample liquid.

13. A particle analyzing apparatus according to claim 12, further comprising means for signalling when said sheath liquid container is not filled with the sheath liquid.

14. A particle analyzing apparatus according to claim 13, further comprising means for compensating for an initial setting value of said sheath liquid container when said sheath liquid container is not filled with the sheath liquid in accordance with the measured sheath liquid level.

15. A particle analyzing apparatus according to claim 14, wherein said measuring means includes a laser source and optically measures the particles to be examined.

16. A particle analyzing apparatus having a pressure control device, comprising:
   particle receiving means for receiving particles to be examined;
   sample supplying means for supplying sample liquid containing particles therein to said particle receiving means;
   a sheath liquid container for storing sheath liquid therein;
   sheath liquid supplying means for supplying the sheath liquid in said sheath liquid container to said particle receiving means;
   convergent stream forming means for generating a thin flow of the sample liquid surrounded by the sheath liquid, with particles included in the sample liquid being individually separated and flowing through said particle receiving means;
   filter means provided in a flow path between said sheath liquid container and said particle receiving means for removing impurities contained in the sheath liquid;
   control means, including a pressure sensor, for controlling pressure of said sheath liquid supplying means so that an output of said pressure sensor is a predetermined value so as to maintain a constant diameter of the converged thin flow;
   signalling means for measuring a level of the sheath liquid in said sheath liquid container and for producing a warning signal when the level of the sheath liquid reaches a predetermined level; and
   measuring means for measuring information of a particle flowing in the converged thin flow at said particle receiving means.

17. A particle analyzing apparatus according to claim 16, wherein said sheath liquid supply means includes pressure regulating means for pressurizing said sheath liquid container, and said signalling means signals said control means when a relative difference between a pressure level applied to said sheath liquid container being filled to capacity with the sheath liquid and a pressure level applied to said sheath liquid container filled to less than capacity becomes higher than a predetermined first value.

18. A particle analyzing apparatus according to claim 17, wherein said measuring means includes a laser source and optically measures the particles to be examined.

19. A particle analyzing apparatus having a pressure control device, comprising:
   particle receiving means for receiving particles to be examined;
   sample supplying means for supplying sample liquid containing particles therein to said particle receiving means;
   a sheath liquid container for storing sheath liquid therein;
   sheath liquid supplying means for supplying the sheath liquid in said sheath liquid container to said particle receiving means;
   convergent stream forming means for generating a thin flow of the sample liquid surrounded by the sheath liquid, with particles included in the sample liquid being individually separated and flowing through said particle receiving means;
   filter means provided in a flow path between said sheath liquid container and said particle receiving means for removing impurities contained in the sheath liquid;
   control means, including a pressure sensor, for controlling pressure of said sheath liquid supplying means so that an output of said pressure sensor is a predetermined value so as to maintain a constant diameter of the converged thin flow;
   signalling means for measuring a clogging level of said filter means and producing a warning signal when the clogging level reaches a predetermined warning level; and
   measuring means for measuring a diameter of a particle flowing in the converged thin flow at said particle receiving means.

20. A particle analyzing apparatus according to claim 19, wherein said sheath liquid supplying means includes pressure regulating means for pressurizing said sheath liquid container, and said signalling means produces the warning signal when an absolute value of the pressure applied to said sheath liquid container becomes higher than a predetermined level.

21. A particle analyzing apparatus according to claim 19, wherein said measuring means includes a laser source and optically measures the particles to be examined.

22. A particle analyzing apparatus having a pressure control device, comprising:
   particle receiving means for receiving particles to be examined;
   sample supplying means for supplying sample liquid containing particles therein to said particle receiving means;
   a sheath liquid container for storing sheath liquid therein;
   sheath liquid supplying means for supplying the sheath liquid in said sheath liquid container to said particle receiving means;
   convergent stream forming means for generating a thin flow of the sample liquid surrounded by the sheath liquid, with particles included in the sample liquid being individually separated and flowing through said particle receiving means;
   filter means provided in a flow path between said sheath liquid container and said particle receiving means for removing impurities contained in the sheath liquid;

control means, including a pressure sensor, for controlling pressure of said sheath liquid supplying means so that an output of said pressure sensor is a predetermined value so as to maintain a constant diameter of the converged thin flow;

signalling means for measuring a level of the sheath liquid in said sheath liquid container and a clogging level of said filter means and for producing a warning signal when either one of said sheath liquid level and said clogging level reaches a predetermined warning level; and measuring means for measuring a diameter of a particle flowing in the converged thin flow at said particle receiving means.

23. A particle analyzing apparatus according to claim 22, wherein said sheath liquid supplying means includes pressure regulating means for pressurizing said sheath liquid container, and said signalling means produces a first warning signal of liquid shortage when a relative difference between a pressure level applied to said sheath liquid container being filled to capacity with the sheath liquid and a pressure level applied to said sheath liquid container filled to less than capacity becomes higher than a first predetermined value and a second warning signal of filter clogging when an absolute value of pressure applied to said sheath liquid container becomes higher than a second predetermined level.

24. A particle analyzing apparatus according to claim 23, wherein said measuring means includes a laser source and optically measures the particles to be examined.

25. A particle analyzing apparatus having a pressure control device, comprising:

particle receiving means for receiving particles to be examined;

sample supplying means for supplying sample liquid containing particles therein to said particle receiving means;

a sheath liquid container for storing sheath liquid therein;

sheath liquid supplying means for supplying the sheath liquid in said sheath liquid container to said particle receiving means;

convergent stream forming means for generating a thin flow of the sample liquid surrounded by the sheath liquid, with particles included in the sample liquid being individually separated and flowing through said particle receiving means;

filter means provided in a flow path between said sheath liquid container and said particle receiving means for removing impurities contained in the sheath liquid;

control means, including a pressure sensor, for controlling pressure of said sheath liquid supplying means so that an output of said pressure sensor is a predetermined value so as to maintain a constant diameter of the converged thin flow;

a control valve provided between said filter means and said particle receiving means for controlling flow of the sheath liquid; and measuring means for measuring information of a particle flowing in the converged thin flow at said particle receiving means.

26. A particle analyzing apparatus according to claim 25, wherein said sheath liquid supplying means includes pressure regulating means for pressurizing said sheath liquid container, and further comprising means for measuring a sheath liquid level on the basis of an output of said pressure sensor obtained when said control valve is closed and a predetermined level of pressure is applied to said sheath liquid container.

27. A particle analyzing apparatus according to claim 26, further comprising means for judging whether said sheath liquid container is filled with said sheath liquid by measuring the liquid level in said sheath liquid container previous to the measurement of the sample liquid.

28. A particle analyzing apparatus according to claim 27, further comprising means for signalling when said sheath liquid container is not filled with the sheath liquid.

29. A particle analyzing apparatus according to claim 28, further comprising means for compensating for an initial setting value of said sheath liquid container when said sheath liquid container is not filled with the sheath liquid in accordance with the measured sheath liquid level.

30. A particle analyzing apparatus according to claim 29, wherein said measuring means includes a laser source and optically measures the particles to be examined.

31. A particle analyzing apparatus having a pressure control device, comprising:

particle receiving means for receiving particles to be examined;

sample supplying means for supplying sample liquid containing particles therein to said particle receiving means;

a sheath liquid container for storing sheath liquid therein;

sheath liquid supplying means for supplying the sheath liquid in said sheath liquid container to said particle receiving means;

convergent stream forming means for generating a thin flow of the sample liquid surrounded by the sheath liquid, with particles included in the sample liquid being individually separated and flowing through said particle receiving means;

sheath liquid level measuring means, including a pressure sensor, for measuring a level of the sheath liquid in said sheath liquid container on the basis of an output of said pressure sensor; and particle measuring means for measuring information of a particle flowing in the converged thin flow at said particle receiving means.

32. A particle analyzing apparatus having a pressure control device, comprising:

particle receiving means for receiving particles to be examined;

sample supplying means for supplying sample liquid containing particles therein to said particle receiving means;

a sheath liquid container for storing sheath liquid therein;

sheath liquid supplying means for supplying the sheath liquid in said sheath liquid container to said particle receiving means;

convergent stream forming means for generating a thin flow of the sample liquid surrounded by the sheath liquid, with particles included in the sample liquid being individually separated and flowing through said particle receiving means;

filter means provided in a flow path between said sheath liquid container and said particle receiving means for removing impurities contained in the sheath liquid;

filter level measuring means, including a pressure sensor, for measuring a clogging level of said filter means on the basis of an output of said pressure sensor; and particle measuring means for measuring information of a particle flowing in the converged thin flow at said particle receiving means.

33. A sheath-flow system for a sample measuring apparatus comprising:

a flow-cell for receiving liquid flowing therethrough;

a sample supplying system, including a pressure source, for supplying a sample liquid to said flow-cell;

a sheath liquid supplying system, including a sheath liquid container for storing sheath liquid therein and a pressure source, for supplying the sheath liquid to said flow-cell by pressurizing said sheath liquid container;

a filter, provided in a flow path between said sheath liquid container and said flow-cell, for removing impurities in the sheath liquid;

a pressure sensor for sensing pressure in said sheath liquid supplying system at a portion between said filter and said flow-cell;

a liquid flow system for forming a thin flow of the sample liquid surrounded by the sheath liquid to flow through said flow-cell; and a control system for controlling the pressure applied to said sheath liquid container so that an output of said pressure sensor is a predetermined value so as to maintain a stable thin flow of the sample liquid flowing through said flow-cell.

34. A particle measuring system having a pressure control device, comprising:

pressure regulating means for regulating pressure in a sheath liquid container containing a sheath liquid and in a sample liquid container containing a sample liquid including particles;

convergent stream forming means for forming a thin flow of the sample liquid surrounded by the sheath liquid, with particles included in the sample liquid being individually separated and flowing one by one in the thin flow;

measuring means for measuring each of the particles flowing in the thin flow;

pressure sensing means for sensing pressure between the sheath liquid container and the converged thin flow and generating a pressure signal;

filter means provided in a flow path between the sheath liquid container and said pressure sensing means for removing impurities in the sheath liquid;

signalling means for detecting a level of the sheath liquid in the sheath liquid container and generating a first warning signal; and control means for controlling said pressure regulating means on the basis of the pressure signal for stabilizing the converged thin flow.

35. A system according to claim 34, wherein said signalling means detects the level of the sheath liquid on the basis of the pressure applied to the sheath liquid container.

36. A system according to claim 34, wherein said signalling means further detects a clogging level of said filter means and generates a second warning signal.

37. A system according to claim 34, wherein said control means further controls said pressure regulating means to stop the pressure on the basis of the first warning signal generated by said signalling means.

38. A system according to claim 34, wherein said convergent stream forming means includes a flow-cell, and the converged thin flow is formed in said flow-cell.

39. A system according to claim 34, wherein the converged thin flow is formed in air.

40. A system according to claim 34, wherein said pressure regulating means comprises a pressure pump, a first regulator provided between said pump and the sample liquid container and a second regulator provided between said pump and the sheath liquid container.

41. A system according to claim 34, wherein said measuring means comprises a light source and an optical device for detecting scattered light or a fluorescence from the particles passing through an inspection portion and irradiated with light from said light source.

42. A system according to claim 34, wherein the sample liquid contained in the sample liquid container includes a blood sample and the particles includes blood cells.

43. A particle measuring system having a pressure control device, comprising:

pressure regulating means for regulating pressure applied to a sheath liquid container containing a sheath liquid and applied to a sample liquid container containing a sample liquid including particles;

convergent stream forming means for forming a thin flow of sample liquid surrounded by the sheath liquid, with particles in the sample liquid being individually separated and flowing one-by-one in the converged thin flow;

measuring means for measuring each of the particles flowing in the thin flow;

pressure sensing means for sensing pressure between the sheath liquid container and the converged thin flow and generating a pressure signal;

signalling means for detecting a level of the sheath liquid in the sheath liquid container and generating a warning signal; and control means for controlling said pressure regulating means on the basis of the pressure signal generated by said pressure sensing for stabilizing the converged thin flow.

44. A system according to claim 43, wherein said signalling means detects the level of the sheath liquid on the basis of the pressure applied to the sheath liquid container.

45. A system according to claim 43, wherein said control means further controls said pressure regulating means to stop pressure on the basis of the warning signal generated by said signalling means.

46. A system according to claim 43, wherein said convergent stream forming means includes a flow-cell, and the converged thin flow is formed in said flow-cell.

47. A system according to claim 43, wherein the converged thin flow is formed in air.

48. A system according to claim 43, wherein said pressure regulating means comprises a pressure pump, a first regulator provided between said pump and the sample liquid container, and a second regulator provided between said pump and the sheath liquid container.

49. A system according to claim 43, wherein said measuring means comprises a light source, and an optical device for detecting scattered light or a fluorescence from the particles passing through an inspection portion and irradiated with light from said light source.

50. A system according to claim 43, wherein the sample liquid contained in the sample liquid container includes a blood sample and the particles include blood cells.

* * * * *

UNITED STATES PATENT AND TRADEMARK OFFICE
CERTIFICATE OF CORRECTION

PATENT NO. : 5,245,318
DATED : September 14, 1993
INVENTOR(S) : Yoshiyuki et al.

It is certified that error appears in the above-indentified patent and that said Letters Patent is hereby corrected as shown below:

COLUMN 2:

Line 48, "makes" should read --to make--.

COLUMN 4:

Line 28, "10" should be deleted.

COLUMN 5:

Line 18, "of," should read --capacity,--.

COLUMN 10:

Line 35, "a diameter" should read --information--.

COLUMN 11:

Line 14, "a diameter" should read --information--.
Line 68, "pressurizing" should read --pressuring--.

UNITED STATES PATENT AND TRADEMARK OFFICE
CERTIFICATE OF CORRECTION

PATENT NO. : 5,245,318
DATED : September 14, 1993
INVENTOR(S) : Yoshiyuki et al.

It is certified that error appears in the above-indentified patent and that said Letters Patent is hereby corrected as shown below:

COLUMN 14:

Line 34, "the" should read --the converged--.
Line 40, "sensing" should read --sensing means--.

Signed and Sealed this

Thirtieth Day of August, 1994

*Attest:*

BRUCE LEHMAN

*Attesting Officer*     *Commissioner of Patents and Trademarks*